(12) United States Patent
Yang et al.

(10) Patent No.: US 12,109,210 B2
(45) Date of Patent: Oct. 8, 2024

(54) METHODS FOR TREATING MAST CELL TUMORS

(71) Applicant: GONGWIN BIOPHARM CO., LTD, Taipei (TW)

(72) Inventors: Chuan-Ching Yang, Taipei (TW); Mao-Yuan Lin, Taipei (TW); Shu-Ying Cheng, Taipei (TW); Yi-Jhen Feng, Taipei (TW)

(73) Assignee: GONGWIN BIOPHARM CO., LTD, Taipei (TW)

( * ) Notice: Subject to any disclaimer, the term of this patent is extended or adjusted under 35 U.S.C. 154(b) by 136 days.

(21) Appl. No.: 17/489,353

(22) Filed: Sep. 29, 2021

(65) Prior Publication Data
US 2023/0098310 A1 Mar. 30, 2023

(51) Int. Cl.
*A61K 31/498* (2006.01)
*A61P 35/00* (2006.01)

(52) U.S. Cl.
CPC ............ *A61K 31/498* (2013.01); *A61P 35/00* (2018.01)

(58) Field of Classification Search
CPC .............................. A61K 31/498; A61P 35/00
See application file for complete search history.

(56) References Cited

U.S. PATENT DOCUMENTS

| | | | | |
|---|---|---|---|---|
| 5,891,454 A * | 4/1999 | Wu | ...................... | A61K 9/0019 514/604 |
| 9,668,990 B1 * | 6/2017 | Yang | ........................ | A61P 35/00 |
| 10,182,998 B2 * | 1/2019 | Yang | ..................... | A61K 9/2004 |
| 10,548,862 B2 * | 2/2020 | Yang | ....................... | A61K 47/10 |
| 11,752,118 B2 * | 9/2023 | Yang | ....................... | A61K 47/34 514/210.16 |
| 12,023,310 B2 * | 7/2024 | Lin | ......................... | A61K 31/18 |
| 2013/0079345 A1 | 3/2013 | Eickhoff et al. | | |
| 2017/0172951 A1 * | 6/2017 | Yang | ...................... | A61K 31/18 |
| 2017/0354621 A1 * | 12/2017 | Wu | ........................ | A61K 47/10 |
| 2018/0055796 A1 * | 3/2018 | Zhong | .................... | A61K 31/18 |
| 2019/0321313 A1 | 10/2019 | Yang et al. | | |
| 2020/0338028 A1 * | 10/2020 | Yang | ..................... | A61K 31/452 |
| 2022/0088038 A1 * | 3/2022 | Wu | ......................... | A61P 43/00 |
| 2022/0168248 A1 * | 6/2022 | Yang | ....................... | A61K 47/10 |
| 2023/0321016 A1 * | 10/2023 | Yang | .................. | A61K 31/4468 424/649 |

(Continued)

FOREIGN PATENT DOCUMENTS

| | | | |
|---|---|---|---|
| CN | 102389410 A | * | 3/2012 |
| CN | 111732575 B | | 12/2020 |
| KR | 102142231 B1 | | 8/2020 |

OTHER PUBLICATIONS

Gao; J. Thorac. Dis. 2013, 5, 472-483. https://doi.org/10.3978/j.issn.2072-1439.2013.08.28 (Year: 2013).*

(Continued)

*Primary Examiner* — Daniel R Carcanague
(74) *Attorney, Agent, or Firm* — Osha Bergman Watanabe & Burton LLP (57) ABSTRACT

Provided is a pharmaceutical composition for treating a mast cell tumor, including a benzenesulfonamide derivative and a pharmaceutically acceptable carrier. Also provided is a method for treating a mast cell tumor in a subject in need thereof by using the pharmaceutical composition.

13 Claims, 4 Drawing Sheets

(56) References Cited

U.S. PATENT DOCUMENTS

2024/0082182 A1* 3/2024 Lin ............... A61K 9/0019
2024/0108592 A1* 4/2024 Wu ............... A61K 39/39558

OTHER PUBLICATIONS

Garrett; Veterinary Medicine: Research and Reports 2014, 5 49-58. htttps://doi.org/10.2147%2FVMRR.S41005 (Year: 2014).*
Guan; Journal of Thoracic Disease 2018, 10, 2448-2455. http://dx.doi.org/10.21037/jtd.2018.03.70 (Year: 2018).*
He; World J. Gastroenterol. 2012, 18, 6861-6864. http://dx.doi.org/10.3748/wjg.v18.i46.6861 (Year: 2012).*
Hsu; Front. Pharmacol. 2018, 9, 1223. https://doi.org/10.3389/fphar.2018.01223 (Year: 2018).*
Li; Lung Cancer 2016, 98, 43-50. https://doi.org/10.1016/j.lungcan.2016.05.012 (Year: 2016).*
Liu; Anticancer Drugs 2015, 26, 1026-1033. https://doi.org/10.1097/cad.0000000000000283 (Year: 2015).*
Gongwin Pharma PTS. (Feb. 26, 2020) [GWA10] The first clinical case of animal trial drug sample PTS field pre-trial-"Canine plantar melanoma" has received good results. [Text and Images] Machine Translation. Facebook. Retrieved Oct. 18, 2022 from https://www.facebook.com/Gongwin6617 (Year: 2020).*
BluePearl Pet Hospital, "Types of Cancer in Dogs" Dated May 4, 2020, 8 pages. Downloaded Dec. 6, 2023 at https://bluepearlvet.com/medical-articles-for-pet-owners/types-of-cancer-in-dogs/ (Year: 2020).*
Miller; Front. Vet. Sci. 2019, 6, 106. https://doi.org/10.3389/fvets.2019.00106 (Year: 2019).*
Virbac AH, Inc .; STELFONTA (tigilanol tiglate injection) Package Insert, dated Aug. 2020, 2 pages. (Year: 2020).*
Valent, Peter et al. "Mast cells as a unique hematopoietic lineage and cell system: From Paul Ehrlich's visions to precision medicine concepts" Theranostics 2020, vol. 10, Issue 23, 10743-10768 (26 pages).
Stone, Kelly D. et al. "IgE, Mast Cells, Basophils, and Eosinophils" J Allergy Clin Immunol. Feb. 2010 ; 125 (16 pages).
Bostock, D. E. et al. "Neoplasms of the Skin and Subcutaneous Tissues in Dogs and Cats" British Veterinary Journal, (1986) 142, 1 (19 pages).
Satdarshan, Monga et al. "Intratumoral Therapy of Cisplatin/Epinephrine Injectable Gel for Palliation in Patients With Obstructive Esophageal Cancer" American Journal of Clinical Oncology: Cancer Clinical Trials American Journal of Clinical Oncology. 23:p. 386-392, Aug. 2000 (17 pages).
Celikoglu, Firuz et al. "Techniques for intratumoral chemotherapy of lung cancer by bronchoscopic drug delivery" Cancer Therapy vol. 6.545-552. 2008 (9 pages).
International Search Report issued in International Application No. PCT/US2022/045244 dated Jan. 25, 2023 (4 pages).
Written Opinion issued in International Application No. PCT/US2022/045244 dated Jan. 25, 2023 (3 pages).

* cited by examiner

METHODS FOR TREATING MAST CELL TUMORS

BACKGROUND

1. Technical Field

The present disclosure relates to pharmaceutical compositions comprising benzenesulfonamide derivatives for treating mast cell tumors, and particularly to methods for treating subjects suffering from mast cell tumors by using the pharmaceutical compositions.

2. Description of Related Art

Mast cells were discovered by Paul Ehrlich in 1879 (Theranostics. 10: 10743-10768, 2020). Mast cells, which develop from bone marrow $CD34^+$ precursor cells, play a role in the immune system and the neuroimmune system. When being activated, mast cells can release inflammatory factors and recruit immune cells. Mast cells are one of common cell types in connective tissue, and present in most tissues around blood vessels and nerves, such as skin, lung mucosa, digestive tract, oral cavity, conjunctiva, and nasal cavity (Journal of Allergy and Clinical Immunology. 125 (2, Supplement 2): S73-S80, 2010).

A mast cell tumor is a round cell tumor composed of mast cells, and it can also refer to aggregation or nodule of mast cells that resembles tumor. A mast cell tumor may occur in humans and many animal species and commonly be found in skin, such as monopathy in trunk or wrist, or sometimes in lungs.

Mast cell tumors are common in dogs and cats, accounting for 16% to 21% in dogs and about 20% in cats of the clinical skin tumor cases. A mast cell tumor is composed of mast cells derived from skin tissue; among these, there are 50% occurring in skin and subcutaneous tissue of body and perineum, 40% occurring in limbs, and 10% occurring in head and neck, and sometimes multiple skin lumps appear at the same time. Clinically, single or multiple tumor lesions can be seen in appearance. Further, tumor cells may invade tissues in the body, such as spleen, liver, lung, and intestine. Clinically, mast cell tumors are more common in middle-aged and elderly individuals (British Veterinary Journal. 142: 1-19, 1986).

Mast cell tumors usually have a large number of tumor cell populations. The tumor cells contain a moderate amount of cytoplasm, in which many small red-purple granules reside. According to Patnaik Grading, mast cell tumors can be classified into three grades: (1) the tumor cells are well differentiated without mitotic phase; (2) the tumor cells are intermediately differentiated, in which the nucleus is large, with a slight pleomorphism and a small amount of mitotic phase; and (3) the tumor cells are poorly differentiated, in which the cells vary in size, large and obvious nucleoli can be found occasionally, cytoplasmic granules are few, and mitosis is vigorous. According to the grade of cellular differentiation and the cellular biologic behavior of tumor cells, the third grade of atypical sclerosing mastocyte proliferation includes: tumor cells invade the subcutaneous tissue, and it can be found in the tumor that the tumor cells vary in size, have large cell nucleus and obvious nucleolus, and are polymorphic and incompletely differentiated. The number of cytoplasmic granules is relatively decreased, which can be stained only by a special dye (e.g., Giemsa, toluidine-blue, and astral blue). Tumorized mast cells usually contain only a small amount of granules, and usually present malignant indicators, including anisocytosis, anisokarycytosis, nuclear poleomorphism, and increased nuclear-to-cytoplasmic ratio. Cytologically, a case of agranular mast cells presenting obvious malignant phase can be regarded as a malignant case.

For the treatment of mast cell tumors, if it is a single and independent lesion, a large-scale surgical resection (at least 3 cm from the edge of the tumor) is performed, and the conditions of the surgical site and the surrounding lymph nodes are regularly determined every 3 months after the operation. For cases that cannot be completely resected or cannot be surgically resected, intratumoral injection of triamcinolone can be considered, but the therapeutic effect is variable. For cases with multiple lesions, treatment with prednisolone in dosages of 2 mg/kg/day for 2 weeks, 1 mg/kg/day for 2 weeks, and 1 mg/kg every other day (once per 48 hours) can be considered, but it may temporarily cause tumor shrinkage or reduced clinical symptoms. For metastatic cases or clinical cases complicated with peptic ulcer, the following drugs can be used to slow down the impact of hyperhistaminemia on the digestive tract: (1) H1 blocker, such as diphenhydramine; (2) H2 blocker, such as cimetidine, famotidine, and ranitidine; and (3) proton pump blocker, such as omeprazole. For clinical peptic ulcer cases, mucosal protective agents such as sucralfate and misoprostol may be helpful in controlling ulcer; further, chemotherapy drugs such as lomustine (CCNU), vinblastine and vincristine may also be effective for these cases.

The clinical prognosis of canine mast cell tumors varies greatly, and the indicator for prognosis is histological grade. Grade I (well differentiation) means a good prognosis (metastasis rate <10%), while Grade III (poor differentiation) means relapses or metastases usually occurring within a few months (metastasis rate is 55% to 96%). The increased cell proliferation markers, such as argyrophilic nucleolar staining organizing regions (AgNOR) and Ki-67 indicate a poor prognosis. The location of tumor is also an indicator for prognosis. The mast cell tumor occurring in groin, perineum, subungual, nasal muzzle, oral cavity, or nasal cavity has high metastasis rate. Variety can also be used as a reference indicator for prognosis; for example, well-differentiated benign tumors are more common in Boxer, while malignant tumors are more common in Chinese Shar Pei.

At present, for the treatment of mast cell tumors, in addition to surgical removal of the tumor, there exists a medication treatment. However, the therapeutic effect of the drugs for dogs has not yet been demonstrated. Therefore, in view of the high incidence of mast cell tumors in pet dogs and cats with serious health threats, there is an unmet need for developing pharmaceutical compositions for the treatment of mast cell tumors that can break through the current technical limitations and meet demands of patients, doctors and veterinarians.

SUMMARY

In view of the foregoing, the present disclosure provides a pharmaceutical composition that is capable of effectively and safely treating mast cell tumors. With the pharmaceutical composition provided in the present disclosure as the treatment or additional treatment of mast cell tumors, amputation or removal of major tissues and organs can be prevented in the case that the interventional therapy cannot be processed, and the life quality of patients or animal patients can be improved.

In at least one embodiment of the present disclosure, a pharmaceutical composition for treating a mast cell tumor is provided. The pharmaceutical composition comprises a benzenesulfonamide derivative and a pharmaceutically acceptable carrier thereof.

In at least one embodiment of the present disclosure, the benzenesulfonamide derivative is represented by formula (I) below:

or a pharmaceutically acceptable salt thereof,
wherein $R_1$ to $R_7$ are independently selected from the group consisting of H, a $C_1$-$C_6$ linear or branched alkyl group, a $C_1$-$C_6$ linear or branched alkoxy group, a $C_3$-$C_6$ cycloalkyl group, a $C_3$-$C_6$ cycloheteroalkyl group, an amino group, and a halo group, or $R_6$ and $R_7$ are linked to each other to form a ring.

In at least one embodiment of the present disclosure, the alkyl, alkoxy, cycloalkyl, and cycloheteroalkyl groups and the ring in $R_1$ to $R_7$ may be independently unsubstituted or substituted with one or more substituents. In some embodiments of the present disclosure, the substituent is selected from the group consisting of phenyl, halo, oxo, ether, hydroxyl, carboxyl, amino, sulfo, and sulfonamide group.

In at least one embodiment of the present disclosure, the benzenesulfonamide derivative is at least one selected from the group consisting of para-toluene sulfonamide, ortho-toluene sulfonamide, meta-toluene sulfonamide, N-ethyl-ortho-toluene sulfonamide, N-ethyl-para-toluene sulfonamide, N-cyclohexyl-para-toluene sulfonamide, -continued and any combination thereof. In some embodiments of the present disclosure, the benzenesulfonamide derivative is para-toluene sulfonamide, ortho-toluene sulfonamide, or meta-toluene sulfonamide.

In at least one embodiment of the present disclosure, the benzenesulfonamide derivative is present in an amount of from about 1% to about 50% by weight of the pharmaceutical composition. In some embodiments of the present disclosure, the pharmaceutical composition further comprises at least one of 1% to 50% by weight of polyethylene glycol (PEG) 400, 1% to 10% by weight of 1,2-propylene glycol, 1% to 10% by weight of sebacic acid, 1% to 20% by weight of 2-ethyl-1,3-hexanediol, 0% to 20% by weight of dimethyl sulfoxide, and 0% to 20% by weight of ethanol.

The present disclosure also provides a method for treating a mast cell tumor in a subject in need thereof, comprising administering a therapeutically effective amount of the above pharmaceutical composition to the subject. In at least one embodiment of the present disclosure, the administering causes ablation of the mast cell tumor.

In at least one embodiment of the present disclosure, the mast cell tumor is a canine mast cell tumor, a feline mast cell tumor, an equine mast cell tumor, a cattle mast cell tumor, or a sheep mast cell tumor.

In at least one embodiment of the present disclosure, the subject is selected from the group consisting of a rodent, a murine, a monkey, a guinea pig, a dog, a cat, a cow, a sheep, a pig, a horse, a rabbit, and a human.

BRIEF DESCRIPTIONS OF THE DRAWINGS

The present disclosure can be more fully understood by reading the following descriptions of the embodiments, with reference made to the accompanying drawings.

DETAILED DESCRIPTION

The following examples are used to exemplify the present disclosure. A person of ordinary skill in the art can understand the other advantages of the present disclosure, based on the specification of the present disclosure. The present disclosure can also be implemented or applied as described in different examples. It is possible to modify and/or alter the following examples for carrying out this disclosure without contravening its scope for different aspects and applications.

It is noted that, as used in this disclosure, the singular forms "a," "an," and "the" include plural referents unless expressly and unequivocally limited to one referent. The term "or" is used interchangeably with the term "and/or" unless the context clearly indicates otherwise.

As used herein, the term "comprising" or "comprises" is used in reference to compositions, methods, and respective component(s) thereof, which are included in the present disclosure, yet open to the inclusion of unspecified elements.

As used herein, the terms "at least one" and "one or more" may have the same meaning and include one, two, three, or more.

Throughout this disclosure, ordinal numbers (e.g., first, second, third, etc.) may be used as an adjective for an element (i.e., any noun in the application). The use of ordinal numbers is not to imply or create an ordering of the elements nor to limit any element to being only a single element unless expressly indicated, such as by the use of the terms "before," "after," "single," and other such terminology. Rather, the use of ordinal numbers is to distinguish between the elements. By way of an example, a first element is distinct from a second element, and the first element may encompass more than one element and succeed (or precede) the second element in an ordering of elements.

As used herein, the term "about" generally means within 10%, 5%, 1%, or 0.5% of a given value or range. Alternatively, the term "about" means within an acceptable standard error of the mean when considered by one of ordinary skill in the art, Unless otherwise expressly specified, all of the numerical ranges, amounts, values and percentages such as those for quantities of materials, durations of time periods, temperatures, operating conditions, ratios of amounts, and the likes disclosed herein should be understood as modified in all instances by the term "about."

As used herein, the term "treat," "treating" or "treatment" encompasses partially or completely preventing, ameliorating, mitigating and/or managing a symptom, a disorder or a condition associated with a disease. The term "treat," "treating" or "treatment" as used herein refers to application or administration of one or more therapeutic agent or surgery to a subject, who has a symptom, a disorder or a condition associated with a disease, with the purpose to partially or completely alleviate, ameliorate, relieve, delay onset of, inhibit progression of, reduce severity of, and/or reduce incidence of one or more symptoms, disorders or conditions associated with the disease. Treatment may be administered to a subject who exhibits only an early sign of such symptoms, disorders, and/or conditions for the purpose of decreasing the risk of developing the symptoms, disorders, and/or conditions associated with a disease.

As used herein, the terms "subject," "individual" and "patient" may be interchangeable and refer to an animal, e.g., a mammal. The term "subject" is intended to refer to both the male and female gender unless one gender is specifically indicated.

As used herein, the term "substituted," when used to describe a chemical structure or moiety, refers to a derivative of that structure or moiety, wherein one or more of its hydrogen atoms is/are substituted with one or more substituent(s). Unless otherwise indicated, a "substituted" structure or moiety has a substituent at one or more substitutable positions of the structure or moiety, and when more than one position in any given structure or moiety is substituted, the substituent is either the same or different at each position.

The present disclosure is directed to a pharmaceutical composition for treating a mast cell tumor in a subject in need thereof, comprising a benzenesulfonamide derivative in a therapeutically effective amount and a pharmaceutically acceptable carrier thereof. The present disclosure is further directed to a method for treating a mast cell tumor in a subject in need thereof, comprising administering a therapeutically effective amount of the pharmaceutical composition of the present disclosure to the subject.

In at least one embodiment of the present disclosure, the benzenesulfonamide derivative is represented by formula (I) below:

(I)

or a pharmaceutically acceptable salt thereof,
wherein $R_1$ to $R_7$ are independently selected from the group consisting of H, a $C_1$-$C_6$ linear or branched alkyl group, a $C_1$-$C_6$ linear or branched alkoxy group, a $C_3$-$C_6$ cycloalkyl group, a $C_3$-$C_6$ cycloheteroalkyl group, an amino group, and a halo group, or $R_6$ and $R_7$ are linked to each other to form a ring, and wherein the alkyl, alkoxy, cycloalkyl, and cycloheteroalkyl groups and the ring in $R_1$ to $R_7$ are independently unsubstituted or substituted with one or more substituents.

In at least one embodiment of the present disclosure, the benzenesulfonamide derivative may be, but not limited to, para-toluene sulfonamide (p-TSA), ortho-toluene sulfonamide, meta-toluene sulfonamide, N-ethyl-ortho-toluene sulfonamide, N-ethyl-para-toluene sulfonamide, N-cyclohexyl-para-toluene sulfonamide, -continued In at least one embodiment of the present disclosure, the benzenesulfonamide derivative is at least one of para-toluene sulfonamide, ortho-toluene sulfonamide, and meta-toluene sulfonamide. The monomer of the benzenesulfonamide derivative is in the form of white crystal. In some embodiments, the pharmaceutical composition comprises a combination of two or more different benzenesulfonamide derivatives in any ratio.

In at least one embodiment of the present disclosure, the pharmaceutically acceptable carrier contained in the pharmaceutical composition of the present disclosure may be at least one selected from the group consisting of a filler, a binder, a preservative, a disintegrating agent, a lubricant, a suspending agent, a wetting agent, a biocompatible solvent, a penetration enhancer, a surfactant, a thickening agent, an acid, a flavoring agent, a complexing agent, and any combination thereof.

In at least one embodiment of the present disclosure, the examples of the binder include, but are not limited to, paste, sorbitol, guar gum, polyvinyl pyrrolidone, cellulose derivatives, such as hydroxypropyl methylcellulose, carboxymethyl cellulose, carbomer (commercially available as Carbopols), and any combination thereof.

In at least one embodiment of the present disclosure, the examples of the preservative include, but are not limited to, sodium benzoate, methyl paraben, propyl paraben, cresol, and any combination thereof.

In at least one embodiment of the present disclosure, the examples of the lubricant include, but are not limited to, metal stearates (such as magnesium stearate, calcium stearate, and sodium stearate), stearic acid, talc, polyethylene glycol, soluble salts (such as sodium chloride and sodium benzoate), and any combination thereof.

In at least one embodiment of the present disclosure, the examples of the wetting agent include, but are not limited to, glycerin, sorbitol, polypropylene glycol, and any combination thereof.

In at least one embodiment of the present disclosure, the examples of the flavoring agent include, but are not limited to, peppermint oil, menthol, lemon oil, orange oil, cinnamon oil, and any combination thereof.

In at least one embodiment of the present disclosure, the pharmaceutically acceptable carrier may be at least one selected from the group consisting of alkylene glycol, sebacic acid, dimethyl sulfoxide (DMSO), ethanol, and any combination thereof. In some embodiments, the examples of the alkylene glycol include, but are not limited to, polyethylene glycol, propylene glycol, hexylene glycol, and any combination thereof.

In at least one embodiment of the present disclosure, the pharmaceutically acceptable carrier is chosen from at least one of 1% to 50% by weight of polyethylene glycol 400, 1% to 10% by weight of 1,2-propylene glycol, 1% to 10% by weight of sebacic acid, 1% to 20% by weight of 2-ethyl-1,3-hexanediol, 0% to 20% by weight of dimethyl sulfoxide, and 0% to 20% by weight of ethanol.

In at least one embodiment of the present disclosure, the benzenesulfonamide derivative is present in an amount of from 1% to 50% of the pharmaceutical composition by weight, such as 1%, 2%, 5%, 10%, 15%, 20%, 25%, 30%, 33%, 35%, 40%, 45%, and 50%. In some embodiments, an amount of the benzenesulfonamide derivative in the pharmaceutical composition has a lower limit chosen from 1%, 5%, 10%, 15%, 20%, and 25% of the composition by weight, and an upper limit chosen from 50%, 45%, 40%, and 35% of the composition by weight. In some embodiments, the benzenesulfonamide derivative is present in an amount of from 20% to 40% of the composition by weight.

In at least one embodiment of the present disclosure, the pharmaceutical composition (GWMC101) provided herein comprises 1% to 50% by weight of para-toluene sulfonamide, 1% to 40% by weight of PEG 400, 1% to 10% by weight of 1,2-propylene glycol, 1% to 5% by weight of sebacic acid, 0% to 15% by weight of para-toluene sulfonic acid, 1% to 20% by weight of 2-ethyl-1,3-hexanediol, 0% to 10% by weight of dimethyl sulfoxide, and 0% to 20% by weight of ethanol.

In at least one embodiment of the present disclosure, a process for preparing the above pharmaceutical composition is also provided. The process comprises: adding and mixing each pharmaceutically acceptable carrier in a predetermined ratio to obtain a first mixture; heating the first mixture to 40° C. to 130° C. under stirring to form a transparent oily liquid; gradually adding the benzenesulfonamide derivative under stirring until being completely dissolved to obtain a second mixture; filtering and cooling the second mixture to obtain the pharmaceutical composition of the present disclosure (GWMC101) in the form of an oily liquid.

The process for preparing an injection formulation of the GWMC101 preparation can be carried out by, for example, adding an adjuvant and/or a solvent to adjust the mixture to be isotonic. Further, the step of filtering in the process can be carried out by, for example, using a microporous filter.

In at least one embodiment of the present disclosure, the pharmaceutical composition may be formulated into a form suitable for the following administration routes: enteral administration, sublingual administration, subcutaneous administration, rectal administration, and parenteral administration, such as subcutaneous injection, intramuscular injection, intravenous injection, intratumoral injection, abdominal injection, intraarterial injection, and subarachnoid injection. In some embodiments of the present disclosure, the pharmaceutical composition may be in a form selected from the group consisting of an injection formulation, a dry powder, a tablet, an oral liquid, a flake, a film, a lozenge, a capsule, a granule, a pill, a gel, a lotion, an ointment, an emulsifier, a paste, a cream, an eye drop, and a salve.

In at least one embodiment of the present disclosure, the pharmaceutical composition may be administered to the subject intratumorally, intravenously, subcutaneously, intradermally, orally, intrathecally, intraperitoneally, intranasally, intramuscularly, intrapleurally, topically, or through nebulization.

In at least one embodiment of the present disclosure, the pharmaceutical composition may be used to treat a mast cell tumor by triggering ablation of the mast cell tumor. For example, the GWMC101 preparation of the present disclosure for triggering ablation of the mast cell tumor may be in the form of an injection formulation and administered to the subject by intratumoral injection. The intratumoral injection dose for mast cell tumor ablation may be from 0.1 mL/injection to 10 mL/injection (about 33 mg to 3,300 mg of para-toluene sulfonamide or other benzenesulfonamide derivatives).

As used herein, the phrase "a therapeutically effective amount" refers to the amount of an active ingredient (e.g., the benzenesulfonamide derivative) that is required to confer a desired therapeutic effect (e.g., triggering ablation of a mast cell tumor) on the treated subject. Effective doses will vary, as recognized by one of ordinary skill in the art, depending on routes of administration, excipient usage, the possibility of co-usage with other therapeutic treatment, and the condition to be treated.

In at least one embodiment of the present disclosure, the benzenesulfonamide derivative administered to the subject is in a therapeutically effective amount of from about 33 mg/day to about 10,000 mg/day, such as from 33 mg/day to 6,600 mg/day, from 165 mg/day to 3,300 mg/day, from 495 mg/day to 3,300 mg/day, from 660 mg/day to 1,650 mg/day, and from 330 mg/day to 1,650 mg/day.

In at least one embodiment of the present disclosure, during a treatment period or a treatment cycle, the therapeutically effective amount of the benzenesulfonamide derivative administered to the subject may range from about 33 mg to about 26,400 mg, such as from 132 mg to 3,300 mg, from 300 mg to 7,000 mg, and from 3,300 mg to 26,400 mg. As used herein, the term "treatment cycle" refers to a treatment period followed by a rest period without treatment that is repeated on a regular schedule.

In at least one embodiment of the present disclosure, the pharmaceutical composition may be administered to the subject 1 to 4 times per day, 1 to 4 times per week, or 1 to 4 times per month. In at least one embodiment of the present disclosure, the pharmaceutical composition may be administered to the subject for a 1- to 4-week or 1- to 4-month treatment period or treatment cycle. In some embodiments, the pharmaceutical composition may be administered to the subject 2 to 3 times per week for a 2-week treatment period. In some embodiments, the pharmaceutical composition is administered to the subject equal to or more than 4 times in the first treatment period.

In at least one embodiment of the present disclosure, the subject to be treated by the method of the present disclosure may be selected from the group consisting of a rodent, a murine, a monkey, a guinea pig, a dog, a cat, a cow, a sheep, a pig, a horse, a rabbit, and a human. In some embodiments, the subject is a dog, a cat, or a human.

In at least one embodiment of the present disclosure, the pharmaceutical composition of the present disclosure is used for treating a mast cell tumor, such as a canine mast cell tumor, a feline mast cell tumor, an equine mast cell tumor, a cattle mast cell tumor, or a sheep mast cell tumor. In some embodiments, the mast cell tumor may be a cutaneous mast cell tumor, such as those occurring in skin, ear, or thorax; or a visceral mast cell tumor, such as those occurring in lung, liver, caecum, lymph, kidney, peritoneum, mammary lobule, spleen, or skeletal muscle.

The present disclosure also provides a use of a pharmaceutical composition in the manufacture of a medicament for treating a mast cell tumor, wherein the pharmaceutical composition comprises a benzenesulfonamide derivative of the present disclosure and a pharmaceutically acceptable carrier thereof.

The following embodiments further demonstrate the efficacy of the current disclosure, but should not be used to limit the scope of the present disclosure.

EXAMPLES

The efficacy of the pharmaceutical composition of the present disclosure for mast cell tumor ablation was clinically evaluated by the following clinical trials.

The clinical trial for the treatment of a mast cell tumor was conducted from January 2020 to December 2020 at the registered animal hospital in Taiwan. The target animals were dogs diagnosed with a mast cell tumor, in which the inclusion and exclusion criteria and the procedure were as follows.

Inclusion Criteria:
- (A) The target animal was greater than 1 (inclusive) year old;
- (B) the target animal was diagnosed as having a mast cell tumor by cytology or histopathology;
- (C) the target animal was evaluated by veterinarian as being not suitable for mast cell tumor resection;
- (D) the target animal had at least one measurable lesion larger than 1 cm in diameter;
- (E) the target animal was evaluated by veterinarian as having a life expectancy longer than 3 months; and
- (F) the owner could understand and abide by the test procedure, and was willing to sign an informed consent form.

Exclusion Criteria:
- (A) The target animal had received systemic chemotherapy within 4 weeks before entering the trial;
- (B) the target animal had received radiotherapy within 4 weeks before entering the trial;
- (C) the target animal had received major operation within 4 weeks before entering the trial (for example, thoracotomy was not allowed, but non-invasive operations, such as biopsy, were allowed);
- (D) the target animal had received any other drugs, biological agents, medical materials or other anti-tumor treatments (such as immunomodulators and radiotherapy) within 4 weeks before entering this trial, or was planned to receive that during the period of this trial;
- (E) the target animal had the following abnormal blood test results before entering this trial: a. hemoglobin; b. absolute neutrophil count (ANC); c. albumin; d. total bilirubin; e. alanine aminotransferase (ALT) and aspartate aminotransferase (AST); and f. chronic kidney disease (CKD) according to International Renal Interest Society (IRIS);
- (F) the target animal had any other serious diseases, and was evaluated by veterinarian as being restricted to participate in this trial;
- (G) the target animal had or was suspected to have allergy to the ingredients contained in the pharmaceutical composition of the present disclosure;
- (H) the lesion was blocked by major blood vessels, and it is difficult to perform intratumoral injection according to the judgment of veterinarian;
- (I) the target animal was pregnant; and
- (J) the target animal had evaluated by veterinarian as being having any unsuitable conditions for participating in this trial.

Treatment Method

The test animal was administered with GWMC101 by intratumoral injection (about 33 mg to about 3300 mg of para-toluene sulfonamide per each injection), in which each intratumoral injection was carried out by multi-point (2 to 6 points) injection.

Electronic vernier caliper measurement was performed before each administration. Tumor volume was determined using the modified ellipsoidal calculation=$\frac{1}{2}\times$length$\times$width$\times$depth (cm) (Monga et al., Intratumoral therapy of cisplatin/epinephrine injectable gel for palliation in patients with obstructive esophageal cancer. American Journal of Clinical Oncology. 23(4): 386-392 (2000); Celikoglu et al., Techniques for intratumoural chemotherapy of lung cancer by bronchoscopic drug delivery. Cancer Therapy. 6: 545-552, (2008)). Otherwise, a computer tomography (CT) scan was performed before the first dosing and at the conclusion visit.

Response Evaluation Criteria

Complete response (CR) means that a measurable or evaluable lesions disappear completely, and no new lesions appear for more than four weeks. Partial response (PR) means that a measurable or evaluable lesions shrinks by more than or equal to 30%, and no new lesions for more than four weeks. Stable disease (SD) means that a measurable or evaluable lesions shrinks by less than or equal to 30% or enlarges by less than or equal to 20%. Progress disease (PD) means that a measurable or evaluable lesion enlarges by more than or equal to 20%, or other lesions deteriorate, and new lesions appear.

Safety Evaluation

When conducting safety evaluation during the trial period, the relevant researchers of the trial are responsible for defining and compiling the adverse events in the protocol (the relevant evaluation method was referred to "Veterinary Cooperative Oncology Group–Common Terminology Criteria for Adverse Events," (VCOG-CTCAE)).

Case No. D01-S06-E06

Case No. D01-S06-E06 is a 12-year-old male old English sheepdog. Before administration, the dog had normal heart function, and the tumor was observed on the elbow of the right foreleg of the dog, which was diagnosed as atypical sclerosis mast cell tumor by the pathological section. The biochemical profile of blood test showed that the dog had normal liver and kidney functions.

Figure 1:
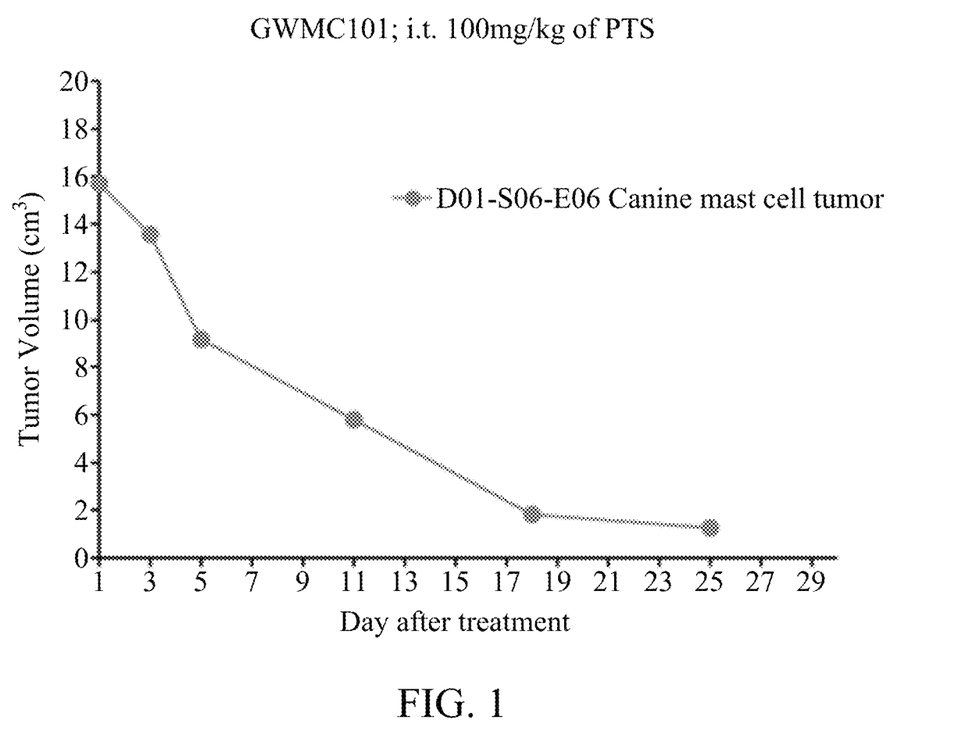
FIG. 1 shows the volume change of mast cell tumors in the lesion of the dog (Case No. D01-S06-E06) treated with the GWMC101 drug, wherein the dosage of PTS in the GWMC101 drug is 100 mg/kg/dog. PTS: para-toluene sulfonamide.
Figure 2A:
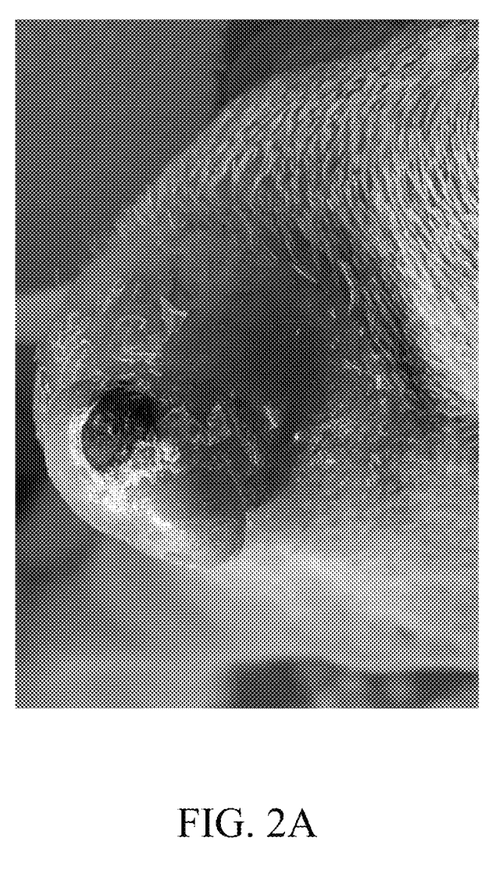
FIGS. 2A to 2C show the representative clinical photographs of mast cell tumors in the lesion of the dog (Case No. D01-S06-E06) before administration of the GWMC101 drug, i.e., Day 1 (FIG. 2A), after the sixth administration, i.e., Day 25 (FIG. 2B), and on the 33$^{rd}$ day after the sixth administration, i.e., Day 53 (FIG. 2C).
Figure 2B:
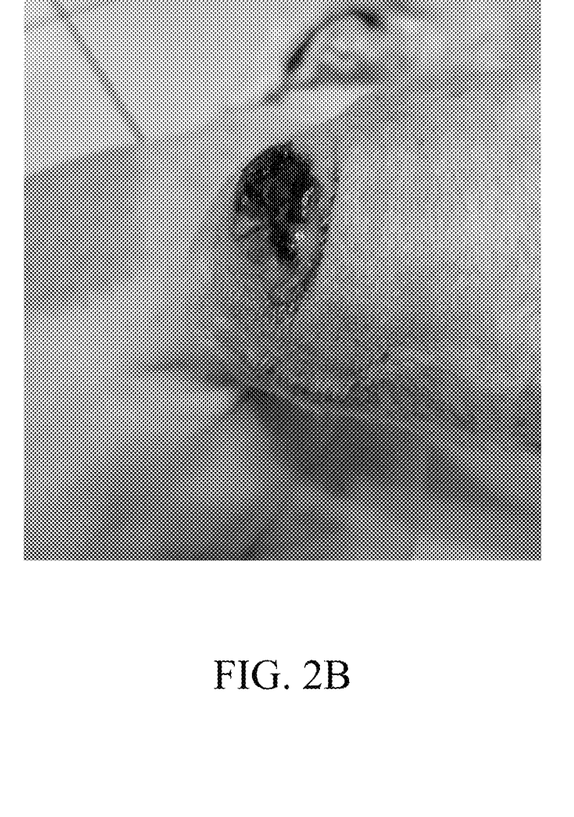
Figure 2C:
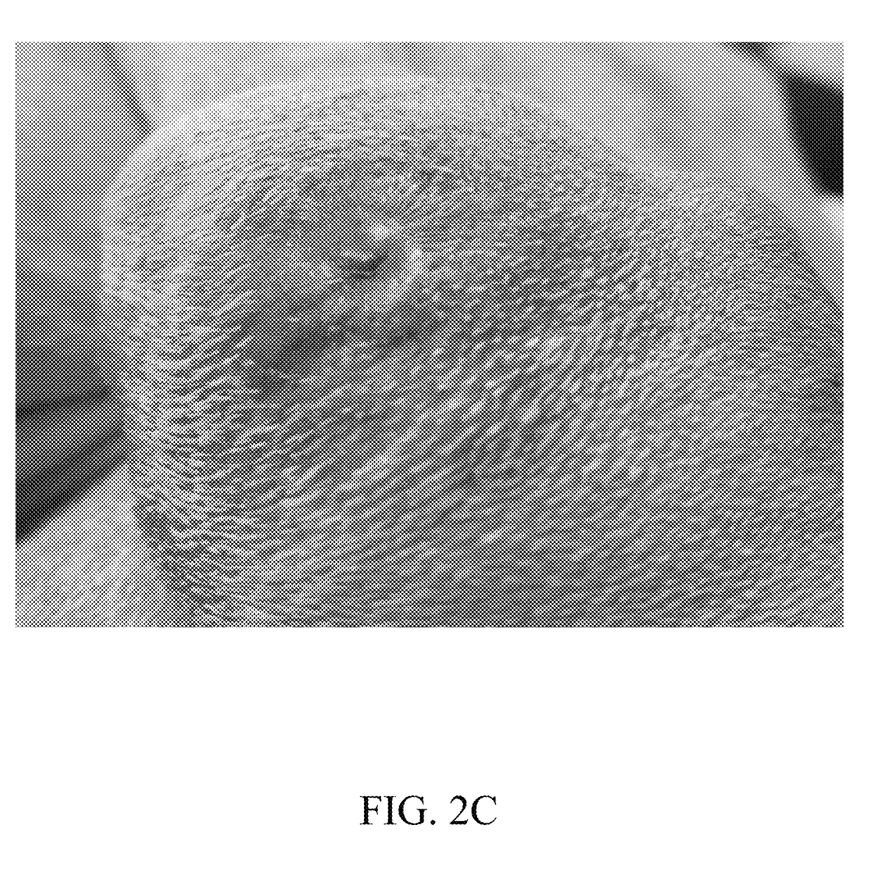

The target lesion was administered by six intratumoral injections (each dose was 0.5 mL to 1.1 mL, with an average of 0.8 mL). The tumor volume was 15.71 cubic centimeters ($cm^3$) before administration (Day 1), and was 1.28 $cm^3$ after the sixth administration (Day 25). According to the statistical results from data measured by the electronic vernier caliper during the treatment period, the tumor size and volume decreased significantly over time. The response rate of the target lesion was assessed by the veterinarian as complete response (CR), and the size of the target tumor reduced by 92%. These results also shown in FIG. 1 and FIGS. 2A to 2C, indicating that the GWMC101 of the present disclosure can reduce the tumor volume of mast cell tumors by 92%. In addition, by the conclusion visit on the 33$^{rd}$ day after the sixth administration of treatment (Day 53), it was found that the site of primary tumor had healed without any signs of tumor.

Adverse Effects

No common side effects such as nausea, vomiting or inflammation were observed. Further, as shown in Table 1 below, the functions of liver and kidney were stable and normal during and after the treatment.

TABLE 1

| Case No. | Visit | Date | GPT* | BUN** |
|---|---|---|---|---|
| 01-S06-E06 | SV | Day 1 | 65 | 23 |
| | T1 | Day 1 | 65 | 23 |
| | T2 | Day 3 | — | — |
| | T3 | Day 5 | — | — |
| | T4 | Day 11 | 65 | 27 |
| | T5 | Day 18 | — | — |
| | T6 | Day 25 | — | — |
| | CV | Day 53 | 78 | 30 |

SV: screening visit
T1 to T6: the 1$^{st}$ to 6$^{th}$ administration of treatment
CV: conclusion visit
GPT: glutamic pyruvic transaminase
BUN: blood urea nitrogen
*Reference range of GPT is 3 U/L to 100 U/L.
**Reference range of BUN is 4.5 U/L to 30.5 mg/dL.

CONCLUSION

The pharmaceutical composition provided in the present disclosure can effectively treat mast cell tumors by promoting the ablation of mast cell tumors, thereby improving the subject's quality of life and clinical symptoms. Furthermore, no significant increase in adverse reactions has been observed in the clinical trials.

While some of the embodiments of the present disclosure have been described in detail above, it is, however, possible for those of ordinary skill in the art to make various modifications and changes to the embodiments shown without substantially departing from the teaching of the present disclosure. Such modifications and changes are encompassed in the scope of the present disclosure as set forth in the appended claims.

What is claimed is:

1. A method for treating a mast cell tumor in a subject in need thereof, comprising administering a therapeutically effective amount of a pharmaceutical composition to the subject, wherein the pharmaceutical composition comprises a benzenesulfonamide derivative and a pharmaceutically acceptable carrier thereof, wherein the benzenesulfonamide derivative is para-toluene sulfonamide, ortho-toluene sulfonamide, or meta-toluene sulfonamide, or a pharmaceutically acceptable salt thereof, wherein the pharmaceutically acceptable carrier is at least one selected from the group consisting of alkylene glycol, sebacic acid, dimethyl sulfoxide, and any combination thereof, and wherein the pharmaceutical composition is administered to the subject by an intratumoral injection.

2. The method of claim 1, wherein the alkylene glycol is at least one selected from the group consisting of polyethylene glycol, propylene glycol, hexylene glycol, and any combination thereof.

3. The method of claim 1, wherein the benzenesulfonamide derivative is present in an amount of from 1% to 50% by weight of the pharmaceutical composition.

4. The method of claim 3, wherein the benzenesulfonamide derivative is present in an amount of from 20% to 40% by weight of the pharmaceutical composition.

5. The method of claim 1, wherein the pharmaceutical composition comprises at least one of 1% to 50% by weight of polyethylene glycol 400, 1% to 10% by weight of 1,2-propylene glycol, 1% to 10% by weight of sebacic acid, 1% to 20% by weight of 2-ethyl-1,3-hexanediol, 0% to 20% by weight of dimethyl sulfoxide, and 0% to 20% by weight of ethanol.

6. The method of claim 1, wherein the administering causes ablation of the mast cell tumor in the subject.

7. The method of claim 1, wherein the mast cell tumor is a canine mast cell tumor, a feline mast cell tumor, an equine mast cell tumor, a cattle mast cell tumor, or a sheep mast cell tumor.

8. The method of claim 1, wherein the mast cell tumor is a cutaneous mast cell tumor or a visceral mast cell tumor.

9. The method of claim 1, wherein the subject is selected from the group consisting of a rodent, a murine, a monkey, a guinea pig, a dog, a cat, a cow, a sheep, a pig, a horse, a rabbit, and a human.

10. The method of claim 1, wherein the benzenesulfonamide derivative in the pharmaceutical composition is administered to the subject in a therapeutically effective amount of from about 33 mg/day to about 10,000 mg/day.

11. The method of claim 1, wherein the benzenesulfonamide derivative in the pharmaceutical composition is administered to the subject in a therapeutically amount of from about 165 mg/day to about 3,300 mg/day.

12. The method of claim 1, wherein the benzenesulfonamide derivative in the pharmaceutical composition is administered to the subject in a therapeutically effective amount of from about 330 mg/day to about 1,650 mg/day.

13. The method of claim 1, wherein the benzenesulfonamide derivative in the pharmaceutical composition is administered to the subject in a therapeutically effective amount of from about 33 mg to about 26,400 mg during a treatment period or a treatment cycle.

* * * * *